(12) United States Patent (10) Patent No.: US 12,610,900 B2

Pei et al. (45) Date of Patent: Apr. 28, 2026

(54) SYSTEM AND METHOD FOR IN-SITU AMELIORATIONREMEDIATION OF SALINE-ALKALI SOIL USING MICROALGAE

(71) Applicant: SHANDONG UNIVERSITY, Jinan (CN)

(72) Inventors: Haiyan Pei, Jinan (CN); Ze Yu, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 647 days.

(21) Appl. No.: 17/973,698

(22) Filed: Oct. 26, 2022

(65) Prior Publication Data

US 2023/0255154 A1 Aug. 17, 2023

(30) Foreign Application Priority Data

Feb. 11, 2022 (CN) .......................... 202210129880.7

(51) Int. Cl.
| | |
|---|---|
| *A01G 33/00* | (2006.01) |
| *A01G 13/32* | (2025.01) |
| *C12M 1/00* | (2006.01) |
| *C12N 1/12* | (2006.01) |

(52) U.S. Cl.
CPC ............. *A01G 33/00* (2013.01); *A01G 13/32* (2025.01); *C12M 21/02* (2013.01); *C12N 1/12* (2013.01)

(58) Field of Classification Search
CPC ........ A01G 33/00; A01G 13/32; A01G 13/33; C12M 21/02
See application file for complete search history.

(56) References Cited

PUBLICATIONS

Chen et al. 2024 (Phycoremediation Potential of Salt-Tolerant *Microalga* Species: Motion, Metabolic Characteristics, and Their Application for Saline-Alkali Soil Improvement in Eco-Farms; Microorganisms 12: 676; https://doi.org/10.3390/microorganisms12040676 (Year: 2024).*

* cited by examiner

*Primary Examiner* — Mary Maille Lyons
(74) *Attorney, Agent, or Firm* — Oliff PLC

(57) ABSTRACT

A system and method for in-situ amelioration of saline-alkali soil using microalgae. Sewage and microalgal seeds are pumped into an microalgae growth pond for growing microalgae, and online equipment is used for monitoring the level of nutrients in the pond. When the microalgae reach the stationary phase of their growth, the screen mesh is lifted to separate microalgae from liquid, so that they are conveniently harvested by scraping. The harvested microalgae are returned to the soil as a soil ameliorant.

7 Claims, 1 Drawing Sheet

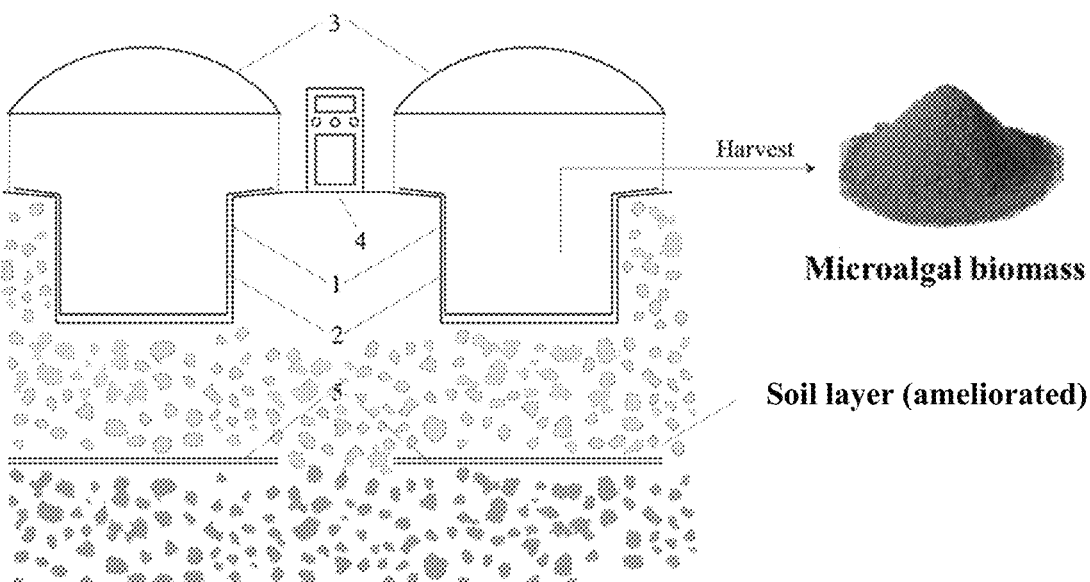

1

SYSTEM AND METHOD FOR IN-SITU AMELIORATIONREMEDIATION OF SALINE-ALKALI SOIL USING MICROALGAE

CROSS-REFERENCES TO RELATED APPLICATIONS

This application claims priority benefits to Chinese Patent Application No. 202210129880.7, filed 11 Feb. 2022, the contents of which are incorporated herein by reference.

TECHNICAL FIELD

The invention relates to the technical field of microorganisms, and in particular, to a system and method for in-situ amelioration of saline-alkali soil using microalgae.

BACKGROUND

Any discussion of the prior art throughout the specification should in no way be considered as an admission that such prior art is widely known or forms part of common general knowledge in the field.

The overall idea of the current method of using microalgae to improve saline-alkali soil is to obtain enough cyanobacterial biomass in an excellent environment in a reactor first, and then make bacterial fertilizer to put into farmland after harvesting, which is time-consuming and laborious, and the improvement effect on saline land is not obvious.

SUMMARY

The invention is to provide a system and method for in-situ amelioration of saline-alkali soil using microalgae.

The invention provides the following technical solutions:

In a first aspect, a system is provided for in-situ amelioration of saline-alkali soil using microalgae. The system comprises a top cover, a microalgae growth pond, a screen mesh, and a soil layer, wherein, the microalgae growth pond is provided with a top opening, and the top cover can be closed over the top opening;

the screen mesh is laid within the microalgae growth pond;

the soil layer is located at least below the microalgae growth pond and to form at least the bottom of the microalgae growth pond;

an impermeable layer is laid underneath the soil layer.

In a second aspect, a method is provided for in-situ amelioration of the saline-alkali soil using microalgae. The method comprises the following steps:

inoculating a microalgae cell solution into a microalgae growth pond, conveying sewage to the microalgae growth pond, and culturing the microalgae;

a large amount of extracellular secretions secreted by the microalgae into the surrounding area during the growth process, which infiltrate into a soil layer below the microalgae growth pond, improving the physicochemical properties of the saline-alkali soil and reshaping the structure of the soil microbial community;

lifting a screen mesh at the end of the microalgae culture cycle, and allowing the screen mesh to stand sufficiently to drain off the water so that the microalgae are trapped on the screen mesh;

scraping the microalgae on the screen mesh for harvesting for subsequent utilization;

after harvesting, the screen mesh is returned to the microalgae growth pond and the microalgae remaining on the screen mesh are used as seed cells for the next culture cycle.

The beneficial effects obtained by one or more embodiments of the present invention are as follows:

(1) Microalgae have the unique advantages of high growth rate and short growth period. During their growth, microalgae excrete plenty of extracellular secretions, which contain large amounts of organic carbon compounds and act as a carbon source for soil microbes and reshape the microbial community structure of the saline-alkali soils. Meanwhile, the extraordinary adaptabilities of microalgae to the high osmotic pressure and pH give them an excellent potential to remediate the saline-alkali soils. Moreover, the ion exchange between the soil layer and the water layer of the microalgae growth pond substantially improves the physicochemical properties of the saline-alkali soils.

Compared to the traditional physicochemical technologies of soil amelioration, the method is simple operation, high efficiency, low cost and free of secondary pollution, and can realize a green and environment-friendly repair process. Compared to the traditional biotechnologies of soil amelioration, the rapid growth rate, short culture period and strong environmental adaptability of microalgae can obviously shorten the period for amelioration of saline-alkali soils. Compared to the current microalga-based technologies, the method integrates in-situ soil amelioration and microalgal cultivation in saline-alkali soils, and reduces the cost of transporting and storing microalgae in the traditional biotechnological processes. Moreover, the method harvests microalgae by use of the cloth mesh, avoiding the energy-intensive harvesting methods (such as centrifugation or pressure filtration, etc.) in traditional harvesting processes, thereby saving on the cost of soil amelioration in saline-alkali soil.

(2) During the process of saline-alkali soil amelioration, microalgae can efficiently capture atmospheric $CO_2$ through their photosynthesis. Theoretically, the rate of carbon fixation of microalgae attains 1.8 g $CO_2$/g microalgae biomass, much higher than that in the traditional salt-tolerant higher plants. Hence, the method also achieves the advantage of carbon reduction while using microalgae for in-situ saline-alkali soil amelioration.

(3) The harvested microalgae biomass can be diversified, and the corresponding metabolites are extracted in a targeted manner according to different contents of the synthetic products in the cells, and downstream processing is performed to produce corresponding high-added-value biological products, such as biodiesel, high-quality microalgae proteins, algal polysaccharides, resistant drugs, food additives, etc., and the benefits thereof can well compensate the cost of saline-alkali soil amelioration, and have good economic feasibility.

BRIEF DESCRIPTION OF THE DRAWINGS

The accompanying drawings, which are incorporated in and constitute a part of the present invention, are included to provide a further understanding of the present invention, and the description of the exemplary embodiments and illustrations of the present invention are intended to explain the present invention and do not constitute improper limits to the present invention.

FIG. 1 is a flow chart of a method for in-situ amelioration of saline-alkali soil using microalgae according to an embodiment of the present invention; wherein,

1: microalgae growth pond; 2: screen mesh; 3: top cover; 4: online monitoring system; 5: impermeable layer.

DETAILED DESCRIPTION

It should be noted that the following detailed description is exemplary and is intended to provide further explanation of the present invention. Unless otherwise specified, all of the technical and scientific terms used in the present invention have the same meaning as commonly understood by ordinary technicians in the art to which the present invention belongs.

As described herein, a system is provided for in-situ amelioration of saline-alkali soil using microalgae. The system comprises a top cover, a microalgae growth pond, a screen mesh, and a soil layer, wherein, the microalgae growth pond is provided with a top opening, and the top cover can be closed over the top opening;

the screen mesh is laid within the microalgae growth pond;

the soil layer is located at least below the microalgae growth pond to form at least the bottom of the microalgae growth pond;

an impermeable layer is laid underneath the soil layer.

The impermeable layer is used to intercept nutrients that have leaked out of the soil layer and to avoid nutrient loss.

In some embodiments, the material of the screen mesh is polyamide (nylon), and a pore diameter of the screen mesh is less than 10 μm. The screen mesh made of polyamide with the pore diameter less than 10 μm is laid within the microalgae growth pond to effectively protect most of the microalgae from infiltrating the soil and prevent the soil particles from entering the microalgae growth pond and creating difficult separation.

In some embodiments, the top cover is made of polymethyl methacrylate or plastic film.

In seasons with little rainfall, the water in the microalgae growth pond tends to evaporate under sunlight, so that it tends to dry out over time, which in turn affects the microalgae culture.

The top cover is made of a transparent material, which allows sunlight to pass through and ensure the normal growth of microalgae. When the top opening of the microalgae growth pond is covered by the top cover, the evaporated water in the microalgae growth pond condenses on the top cover and flow back into the microalgae growth pond, which effectively prevents the evaporation of water from the microalgae growth pond and ensures the normal growth of microalgae over a longer period of time.

In some embodiments, a depth of the microalgae growth pond is 15-20 cm.

In some embodiments, a thickness of the soil layer is 20-40 cm, preferably 30 cm.

A method is provided for in-situ amelioration of the saline-alkali soil using microalgae. The method comprises the following steps:

inoculating a microalgae cell solution into a microalgae growth pond, conveying sewage to the microalgae growth pond, and culturing the microalgae;

a large amount of extracellular secretions secreted by the microalgae into the surrounding area during the growth process, which infiltrate into a soil layer below the microalgae growth pond, improving the physicochemical properties of the saline-alkali soil and reshaping the structure of the soil microbial community;

lifting a screen mesh at the end of the microalgae culture cycle, and allowing the screen mesh to stand sufficiently to drain off the water so that the microalgae are trapped on the screen mesh;

scraping the microalgae on the screen mesh for harvesting for subsequent utilization;

after harvesting, the screen mesh is returned to the microalgae growth pond and the microalgae remaining on the screen mesh are used as seed cells for the next culture cycle.

In some embodiments, an initial biomass concentration in the microalgae growth pond is 0.2-0.5 g/L.

Further, a culture period is 6-10 days.

In some embodiments, a concentration of each nutrient in the microalgae growth pound is monitored online during the culturing of the microalgae.

The present invention will be further described below in conjunction with the examples.

Example 1

Amelioration of saline-alkali soils in a coastal area in Shandong Province.

The specific process is shown in FIG. 1. The system for amelioration of saline-alkali soils comprises a microalgae growth pond 1, a screen mesh 2, a top cover 3, saline-alkali soils and an impermeable layer 5. Wherein, the microalgae growth pond is formed by the saline-alkali soils; the screen mesh 2 is laid within the microalgae growth pond 1 and has a pore diameter less than 10 μm to trap microalgae and hold the saline-alkali soils outside the microalgae growth pond; the system is connected to the sewage source and the microalgae growth pond via a sewage pipeline; the top cover 3 is made of transparent material and is used to close the top opening of the microalgae growth pond 1. The system uses an online monitoring system 4 to monitor the nitrogen, phosphorus, salinity, alkalinity, pH, DO and microalgae biomass concentration of the sewage in the microalgae growth pond in real time and to fine-tune the nutrients in the microalgae growth pond at any time based on the real time data to ensure the growth of microalgae cells in the microalgae growth pond. Soil data such as salinity, alkalinity, organic matter, nitrogen and phosphorus are regularly monitored to determine the restoration cycle.

Step (1): Cultivation of Microalgae Seeds Solution:

The *Spirulina subsalsa* was selected as the algae species, the standard *Spirulina* medium (SP medium) was selected for growing the algal seeds of *Spirulina subsalsa*. The components of SP medium were shown in Table 1.

TABLE 1

| Component | Dosage |
| --- | --- |
| $NaHCO_3$ | 13.61 g/L |
| $Na_2CO_3$ | 4.03 g/L |
| $K_2HPO_4$ | 0.50 g/L |
| $NaNO_3$ | 2.50 g/L |
| $K_2SO_4$ | 1.00 g/L |
| NaCl | 1.00 g/L |
| $MgSO_4 \cdot 7H_2O$ | 0.20 g/L |
| $CaCl_2 \cdot 2H_2O$ | 0.04 g/L |
| $FeSO_4 \cdot 7H_2O$ | 0.01 g/L |
| A5 (Trace metal solution*) | 1 mL/L |

*The components of A5 are shown in Table 2.

TABLE 2

| Components | Dosage* |
|---|---|
| $H_3BO_3$ | 2.86 g/L $dH_2O$ |
| $MnCl_2 \cdot 4H_2O$ | 1.86 g/L $dH_2O$ |
| $ZnSO_4 \cdot 4H_2O$ | 0.22 g/L $dH_2O$ |
| $Na_2MoO_4 \cdot 2H_2O$ | 0.39 g/L $dH_2O$ |
| $CuSO_4 \cdot 6H_2O$ | 0.08 g/L $dH_2O$ |
| $Co(NO_3)_2 \cdot 6H_2O$ | 0.05 g/L $dH_2O$ |

*The abbreviation "$dH_2O$" stands for distilled water.

The culture was incubated in a volume of 100 L at 25° C. under 24 hours of continuous light (intensity 2500 Lux) for 10 days. After the culture was finished, standing for a period of time, and then harvesting the *Spirulina subsalsa*.

Step (2): Construction of the Microalgae Growth Pond:

The microalgae growth pond was built from the saline-alkali soils, with a size of 1 m in length, 0.5 m in width, and 0.2 m in depth, an effective volume of the microalgae growth pond is 0.1 m³, wherein a screen mesh, with a pore diameter of 6.5 μm, was laid within the microalgae growth pond. A soil layer of 0.3 m depth or thickness below the bottom or outside the side walls of the microalgae growth pond is the soil layer to be ameliorated and an impermeable layer is laid outside the soil layer to be ameliorated. About 80 L of sewage water was pumped into the microalgae growth pond covered with a transparent top cover made of polymethyl methacrylate.

Step (3): Culture of Microalgae:

The *Spirulina subsalsa* harvested in Step (1) was inoculated into the microalgae growth pond in Step (2) with an initial biomass concentration of 0.4 g/L and incubated for 9 days. The sewage had an initial nitrogen concentration of 250 mg/L, an initial phosphorus concentration of 7 mg/L, an initial salinity concentration of 0.1%, an initial pH value of 7.5 and an initial DO value of 6 mg/L.

Step (4): Harvesting of Microalgal Biomass

After 9 days of cultivation, lifting the nylon screen mesh and allowing the screen mesh to stand sufficiently to drain off the water, scraping the *Spirulina subsalsa* trapped in the screen mesh into a sterile container and storing in a −20° C. refrigerator. The *Spirulina subsalsa* remaining in the screen mesh together with the screen mesh were returned to the microalgae growth pond in step (2) as the initial algae species for the second culture cycle, and the newly cultured *Spirulina subsalsa* species from step (1) was added and the initial biomass concentration in the microalgae growth pond was adjusted to 0.4 g/L to start the second culture cycle.

Step (5): Resource Utilisation of Microalgae:

The *Spirulina subsalsa* harvested in step (4) was freeze-dried to constant weight in a freeze-dryer and fully ground into a powder, which was measured using spectrophotometry at 10% *Spirulina* cyanobacteria content.

The *Spirulina subsalsa* harvested in step (4) was freeze-dried to a constant mass in a freeze dryer and fully ground to a powder. The content of *Spirulina* phycocyanin was measured to be 10% using spectrophotometric methods, which can be used for the production of *Spirulina* phycocyanin.

After 3-5 culture cycles, the soil conductivity was decreased by 22%, the soil salinity was reduced by 20%, 80 g of the *Spirulina* powder was harvested, and 5 g of the *Spirulina* phycocyanin was extracted The foregoing descriptions are merely preferred embodiments of the present invention, and are not intended to limit the present invention. For a person skilled in the art, the present invention may have various modifications and changes. Any modification, equivalent replacement, or improvement made without departing from the spirit and principle of the present invention shall fall within the protection scope of the present invention.

What is claimed is:

1. A system for in-situ amelioration of saline-alkali soil using microalgae, comprising a top cover, a microalgae growth pond, a screen mesh, a soil layer, and an impermeable layer, wherein:

the top cover covers a top opening of the microalgae growth pond, the microalgae growth pond being for culturing the microalgae;

the screen mesh is disposed within the microalgae growth pond and on top of a bottom portion of the microalgae growth pond, and the screen mesh drains off water when the screen mesh is lifted so that the microalgae are trapped on the screen mesh at an end of a microalgae culture cycle;

the soil layer is disposed below the screen mesh, wherein extracellular secretions secreted by the microalgae have infiltrated into the soil layer below the microalgae growth pond, and have reshaped a structure of a soil microbial community; and the impermeable layer is disposed under the soil layer.

2. The system according to claim 1, wherein the screen mesh is made of polyamides, and a pore diameter of the screen mesh is less than 10 μm.

3. The system according to claim 1, wherein the top cover is made of polymethyl methacrylate or plastic film.

4. The system according to claim 1, wherein a depth of the microalgae growth pond is 15-20 cm.

5. The system according to claim 1, wherein a thickness of the soil layer is 20-40 cm.

6. The system according to claim 5, wherein the thickness of the soil layer is 30 cm.

7. The system according to claim 1, wherein the extracellular secretions secreted by the microalgae are extracellular polymeric substances.

* * * * *